US00PP21986P2

(12) United States Plant Patent
Giesen

(10) Patent No.: US PP21,986 P2
(45) Date of Patent: Jun. 21, 2011

(54) *SOLENOSTEMON* PLANT NAMED 'MOS THIMINT'

(50) Latin Name: *Solenostemon scutellarioides*
Varietal Denomination: Mos Thimint

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/803,822

(22) Filed: Jul. 7, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — June Hwu
*Assistant Examiner* — Louanne Krawczewicz Myers
(74) *Attorney, Agent, or Firm* — S. Matthew Edwards

(57) ABSTRACT

A new *Solenostemon* plant named 'Mos Thimint' particularly distinguished by the yellow-green and purple colored foliage with an upright, well branched and uniform plant habit.

1 Drawing Sheet

Latin name of the genus and species of the plant claimed: *Solenostemon scutellarioides.*

Varietal denomination: 'Mos Thimint'.

BACKGROUND OF THE NEW PLANT

The present invention comprises a new *Solenostemon,* botanically known as *Solenostemon scutellarioides,* and hereinafter referred to by the variety name 'Mos Thimint'.

'Mos Thimint' is a product of a planned breeding program. The new cultivar has yellow-green and purple colored foliage, with an upright, well branched and uniform plant habit.

'Mos Thimint' originated from a hybridization made in January 2006 in a controlled breeding environment in Andijk, Netherlands. The female parent was the unpatented, proprietary plant designated 'CS06-1-1' with smaller, lighter foliage and a longer stem length.

The male parent of 'Mos Thimint' was the unpatented, proprietary plant designated as 'CS06-4-1' with longer stem length, fewer serrations, and thinner stems. The resultant seed was sown in July 2006.

'Mos Thimint' was selected as one plant within the progeny of the stated cross in September, 2006 in a controlled environment in Andijk, The Netherlands.

The first act of asexual reproduction of 'Mos Thimint' was accomplished when vegetative cuttings were propagated from the initial selection in September 2006 in a controlled environment in Andijk, Netherlands.

BRIEF SUMMARY OF INVENTION

Horticultural examination of plants grown from cuttings of the plant initiated in September 2006, and continuing thereafter, has demonstrated that the combination of characteristics as herein disclosed for 'Mos Thimint' are firmly fixed and are retained through successive generations of asexual reproduction.

'Mos Thimint' has not been observed under all possible environmental conditions. The phenotype may vary significantly with variations in environment such as temperature, light intensity and day length.

Plant Breeders' Rights for this cultivar were applied for in Canada on Feb. 18, 2010 (#10-6845) and in Switzerland on Apr. 15, 2010 (#10-2643). 'Mos Thimint' has not been made publicly available more than one year prior to the filing of this application.

The following traits have been repeatedly observed and are determined to be basic characteristics of the new variety. The combination of these characteristics distinguishes this *Solenostemon* as a new and distinct variety.

BRIEF DESCRIPTION OF THE PHOTOGRAPHS

The accompanying photographic drawing shows typical foliage characteristics of 'Mos Thimint' with colors being as true as possible with an illustration of this type. The photographic drawing shows a potted plant of the new variety.

DETAILED BOTANICAL DESCRIPTION

The plant descriptions, measurements and aforementioned photographs were taken in early April 2010 in Gilroy, Calif. in a greenhouse. Plants were approximately 10-12 weeks of age and were growing in a 4 inch pot.

Color references are made to The Royal Horticultural Society Colour Chart (R.H.S.) 2001.

TABLE 1

DIFFERENCES BETWEEN THE NEW VARIETY 'MOS THIMINT' AND A SIMILAR VARIETY

| | 'Mos Thimint' | 'Daffy' (Commercially known as 'Stained Glassworks Daffy', unpatented) |
|---|---|---|
| Foliage margin type: | More serrate | Less serrate |
| Foliage margin color: | Yellow-green | Green |
| Plant habit: | More compact and upright | Less compact or upright |

Plant:

*Form, growth and habit.*—Annual potted or garden plant grown for its distinctive and colorful foliage;

Stems strong, upright and freely branching; moderately vigorous growth habit.

*Plant height.*—30-33 cm.

*Plant width.*—50-58 cm.

*Garden performance and tolerance to weather.*—Very good.

Roots:

*Number of days to initiate roots.*—About 4 days at about 22 degrees C.

*Number of days to produce a rooted cutting.*—6-8 at 22 degrees C.

*Type.*—Fine, fibrous, free branching.

*Color.*—RHS N155B but whiter.

Foliage:

*Arrangement.*—Opposite, simple.

*Immature, leaf color, upper surface.*—Closest to RHS 187A but a darker more velvety hue; with between RHS 144A and RHS 146A margins.

*Immature, leaf color, lower surface.*—Closest to RHS 147B.

*Mature, leaf color, upper surface.*—Closest to RHS N77A but deeper-darker and less velvety looking and becoming blotchy towards the margins; with lighter than RHS 146A margins of about 0.3-0.5 cm wide.

*Mature, leaf color, lower surface.*—Closest to RHS 147B.

*Length.*—8.7-10.2 cm.

*Width.*—5.2-5.5 cm.

*Shape.*—Ovate.

*Base shape.*—Attenuate.

*Apex shape.*—Acuminate.

*Margin.*—Crenate to almost serrate.

*Texture, upper surface.*—Pubescent; lightly hirsute.

*Texture lower surface.*—Pubescent; lightly hirsute.

*Color of veins, upper surface.*—RHS 183C.

*Color of veins, lower surface.*—RHS 147C.

*Petiole color.*—RHS 144A.

*Petiole length.*—3.5-4.0 cm.

*Petiole diameter.*—0.3 cm.

*Petiole texture.*—Pubescent.

Stem:

*Color of stem.*—Between RHS 146A and RHS 146B.

*Length of stem.*—29-32 cm.

*Diameter.*—0.7 cm.

*Length of internodes.*—2.5-10.5 cm.

*Texture.*—Pubescent.

Inflorescence: Flowering development was not observed on this plant to this date. Therefore also, seed development has not been observed.

Disease/pest resistance: Disease/pest resistance has not been observed on this hybrid.

What is claimed is:

1. A new and distinct variety of *Solenostemon* plant named 'Mos Thimint' substantially as illustrated and described herein.

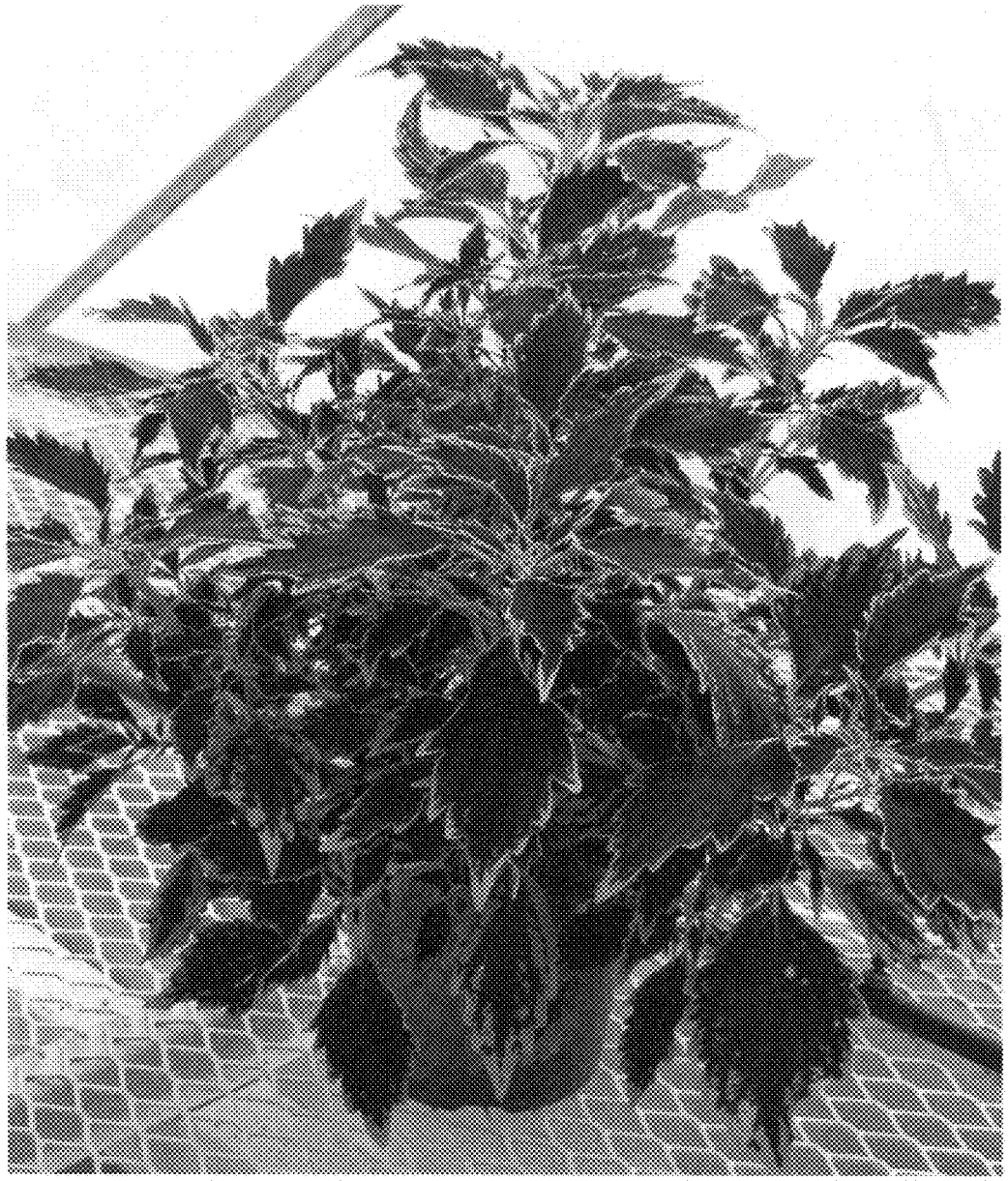

* * * * *